(12) United States Patent
Le Court

(10) Patent No.: US 11,819,448 B2
(45) Date of Patent: Nov. 21, 2023

(54) GROOVED MENSTRUAL CUP, PRODUCTION METHOD THEREOF, AND ASSOCIATED DISINFECTION METHOD AND KIT

(71) Applicant: CLARIPHARM, Saint Alban (FR)

(72) Inventor: Clarisse Le Court, Pleneuf Val Andre (FR)

(73) Assignee: CLARIPHARM, Saint Alban (FR)

( * ) Notice: Subject to any disclaimer, the term of this patent is extended or adjusted under 35 U.S.C. 154(b) by 969 days.

(21) Appl. No.: 16/634,853

(22) PCT Filed: Jul. 27, 2018

(86) PCT No.: PCT/FR2018/051934
§ 371 (c)(1),
(2) Date: Jan. 28, 2020

(87) PCT Pub. No.: WO2019/020958
PCT Pub. Date: Jan. 31, 2019

(65) Prior Publication Data
US 2023/0132920 A1 May 4, 2023

(30) Foreign Application Priority Data

Jul. 28, 2017 (FR) ...................................... 1770805

(51) Int. Cl.
*A61F 5/455* (2006.01)

(52) U.S. Cl.
CPC .................................. *A61F 5/4553* (2013.01)

(58) Field of Classification Search
CPC ...................................................... A61F 5/4553
See application file for complete search history.

(56) References Cited

U.S. PATENT DOCUMENTS

| | | | | |
|---|---|---|---|---|
| 3,845,766 A | * | 11/1974 | Zoller | A61F 5/4553 D24/141 |
| 5,295,984 A | | 3/1994 | Contente et al. | |
| 5,827,248 A | * | 10/1998 | Crawford | A61F 5/4553 604/328 |
| 5,947,992 A | * | 9/1999 | Zadini | A61F 5/4553 606/191 |
| 2002/0010443 A1 | * | 1/2002 | Zadini | A61F 13/202 604/322 |

(Continued)

FOREIGN PATENT DOCUMENTS

FR      2187280 A1    1/1974
GB      2425260 A    10/2006

*Primary Examiner* — Susan S Su
*Assistant Examiner* — Ted Yang
(74) *Attorney, Agent, or Firm* — Craft Chu PLLC; Andrew W. Chu

(57) ABSTRACT

The menstrual cup includes an upper opening and a receptacle having a body with a curved longitudinal shape and a base. The cup extends longitudinally from the opening to the base and has an inner surface corresponding to the concave portion of the receptacle, and an outer surface corresponding to the convex portion of the receptacle. The body includes at least one hollow longitudinal groove on the inner surface of the body and at least one solid longitudinal groove on the outer surface of the body, aligned with the hollow longitudinal groove on the inner surface. The invention also relates to an associated kit and a method for disinfecting the menstrual cup.

11 Claims, 2 Drawing Sheets

(56) References Cited

U.S. PATENT DOCUMENTS

| | | | |
|---|---|---|---|
| 2008/0125692 A1* | 5/2008 | Feemster | A61F 6/08 604/15 |
| 2020/0375788 A1* | 12/2020 | Zhang | A61F 5/4553 |
| 2021/0069009 A1* | 3/2021 | Im | A61F 5/4553 |
| 2021/0113363 A1* | 4/2021 | Evans | A61F 5/4553 |
| 2022/0331148 A1* | 10/2022 | Miller | A61F 5/4404 |
| 2022/0409423 A1* | 12/2022 | Priya Ranjan | A61F 5/451 |

* cited by examiner

GROOVED MENSTRUAL CUP, PRODUCTION METHOD THEREOF, AND ASSOCIATED DISINFECTION METHOD AND KIT

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

This invention concerns a menstrual cup and a corresponding production process. The invention also concerns a disinfection method of the menstrual cup.

2. Description of Related Art Including Information Disclosed Under 37 CFR 1.97 and 37 CFR 1.98

The menstrual cycle of post-puberty women involves flows of menstrual blood periodically, generating comfort and convenience problems.

A first known solution is using sanitary napkins or tampons. Another alternative solution has been proposed, and is based on the use of menstrual cups, namely, devices in the shape of recipients inserted into the vaginal cavity in order to collect menstrual blood flows.

Unfortunately, some users may have so-called abundant periods, that is, a flow stream greater than the statistical norm. These abundant periods may exceed the containment capacity of the menstrual cup during the maximal duration of use and may spill out of it.

BRIEF SUMMARY OF THE INVENTION

Thus, a first goal of this invention is to propose a menstrual cup in which the containment capacity is increased without significantly increasing the maximal diameter of the menstrual cup.

In addition, for users having tonicity impairments of perineum or of the vaginal wall or weakening of them, maintaining the menstrual cup in place may be compromised, which may lead here also to displacements of the menstrual cup and undesired flows. In fact, the more the perineum is weakened, the less easy it is to maintain the menstrual cup in place in the vaginal cavity. As a result, there may be blood leakage because the walls of the vagina are not going to clamp the menstrual cup well.

Thus, a second goal of this invention is to propose a menstrual cup that can counteract the tonicity impairments of the perineum or the vaginal wall or their weakening.

In order to overcome the problems of the prior art, the invention proposes a menstrual cup including an upper opening, and a receptable including a body in a curved longitudinal shape and a base, the cup extending longitudinally from the opening to the base and having an internal surface in the concavity of the receptacle, and an external surface in the convexity of the receptacle.

As per a first feature, the body includes at least one hollow longitudinal groove on the internal surface of the body.

Advantageously, the hollow longitudinal groove allows increasing the containment capacity of the menstrual cup without increasing the size of the menstrual cup.

As per other features taken in isolation or combined as per all technically feasible combinations:
- the cup includes a number of hollow and/or solid longitudinal grooves; and/or
- said hollow grooves with which the solid grooves overlap are distributed regularly on the periphery of the body; and/or
- the cup includes four hollow grooves that match four solid grooves; and/or
- the cup includes at least one groove having a curved or angular shape; and/or
- the cup includes at least one groove having a general flared shape, in the shape of a pear or ovoid; and/or
- the cup includes at least one groove having a general serpentine shape; and/or
- at least one groove has a sectional tubular shape corresponding to around one third of that of the opening; and/or
- the cup includes a flared section towards the top between the body and the opening; and/or
- said flared section has an increase of diameter of at least around 25% between the maximal diameter of the body and the external diameter of the flared section.

The invention also concerns a kit including a menstrual cup as per the invention configured to be resistant to microwaves, and a storage container resistant to microwaves.

Another aim of the invention concerns a production process of a menstrual cup as per the invention, including a forming step of at least one solid longitudinal groove and at least one hollow longitudinal groove, typified by a shaping of said grooves through a mold including a matching solid longitudinal groove.

The invention also concerns a disinfection method of a menstrual cup as per the invention, configured to be resistant to microwaves, the method including preferably at least one cleaning step of the menstrual cup; a step of placement of the menstrual cup in a storage container resistant to microwaves; and a step of application to microwaves on the cup and the container so as to disinfect the menstrual cup.

BRIEF DESCRIPTION OF THE SEVERAL VIEWS OF THE DRAWINGS

The invention will be more detailed by the description of the non-limiting embodiments, and on the basis of the appended figures.

DETAILED DESCRIPTION OF THE INVENTION

Figure 1:
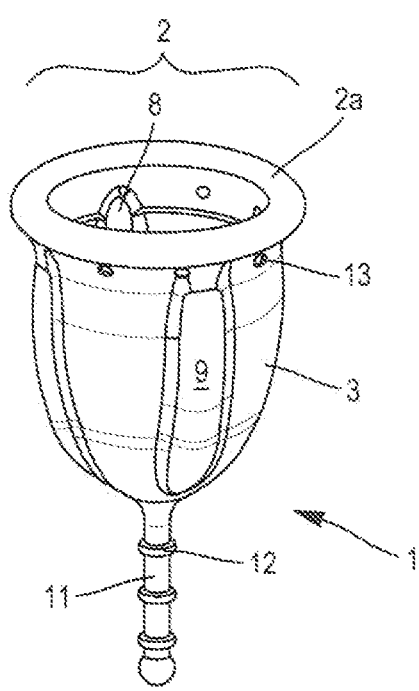
FIG. 1 is a perspective view into the space of a menstrual cup as per a first variant of the invention.
Figure 2:
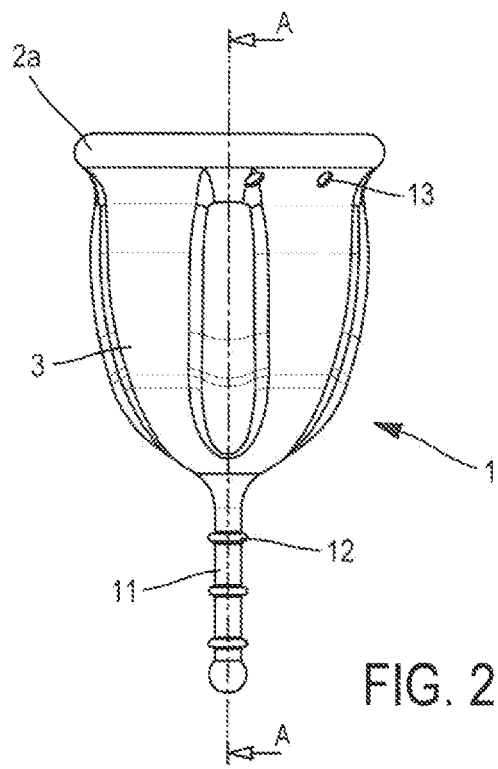
FIG. 2 is a side elevation view of the menstrual cup of FIG. 1.
Figure 3:
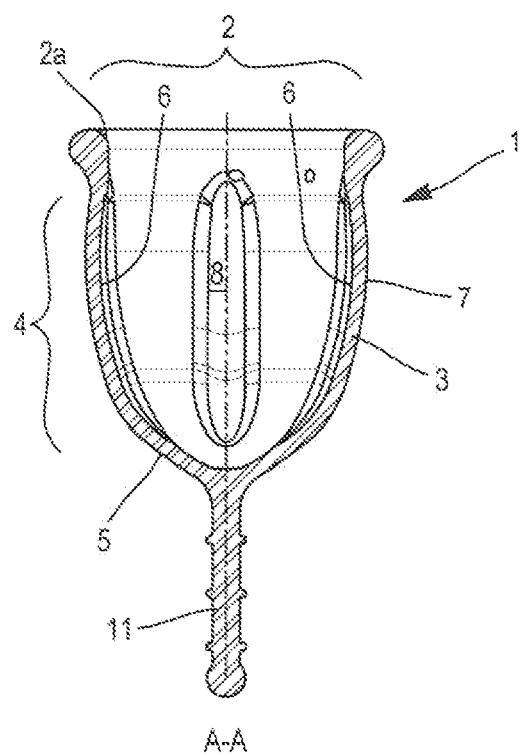
FIG. 3 is a sectional view as per AA of the menstrual cup of FIG. 2.
Figure 4:
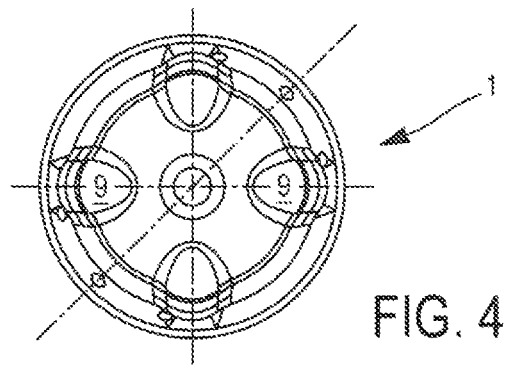
FIG. 4 is a bottom plan view from below of the menstrual cup of FIGS. 1 through 3.
Figure 9:
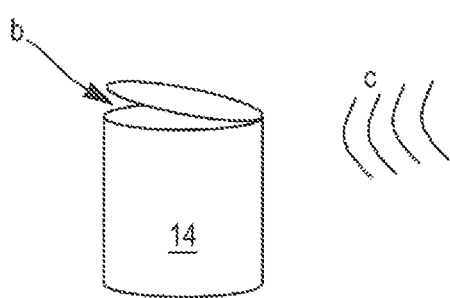
FIG. 9 is a schematic view into the space illustrating the disinfection method as per the invention.
Figure 5:
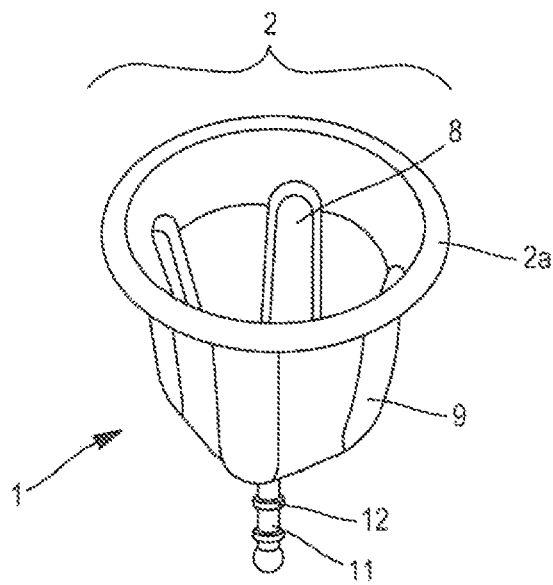
FIG. 5 is a perspective view into the space of a menstrual cup as per a second variant of the invention.
Figure 6:
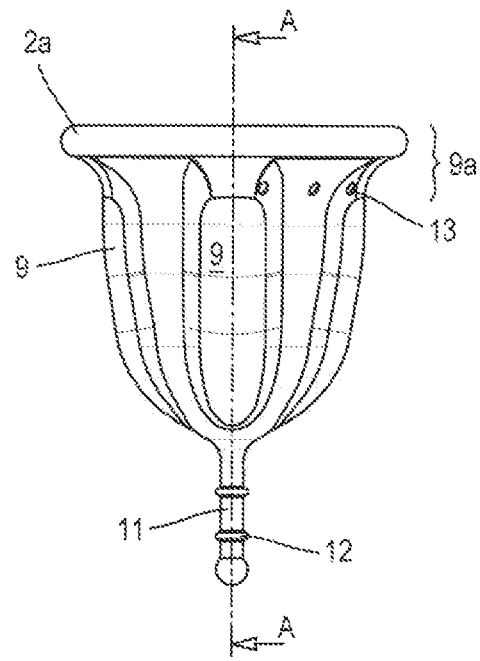
FIG. 6 is a side elevation view of the menstrual cup of FIG. 5.
Figure 7:
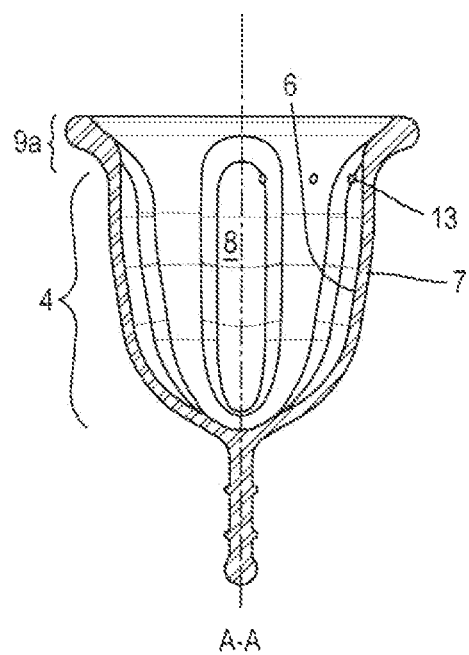
FIG. 7 is a sectional view as per AA of the menstrual cup of FIG. 6.
Figure 8:
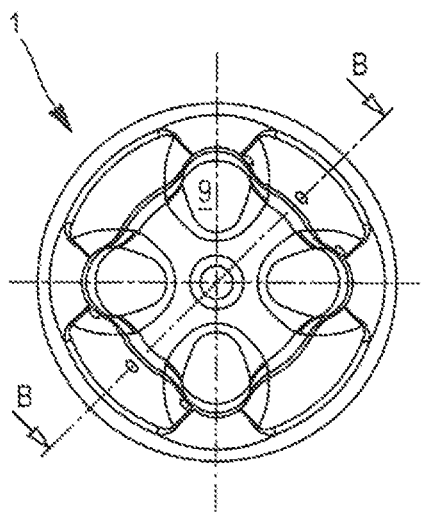
FIG. 8 is a bottom plan view from below of the menstrual cup of FIGS. 5 through 7.

This invention concerns a menstrual cup 1 improved in comparison to the prior art.

The menstrual cup 1 includes an upper opening 2, and a receptacle 3. The upper opening 2 is delimited by a flange 2a. Receptacle 3 has a container shape and is configured to contain the menstrual flows arriving through opening 2. The section of opening 2 and/or the section of receptacle 3 may be of any shape, for example in a polygonal shape such as a square, rectangular, triangular, trapezoidal shape, or a curved shape, such as circle shape or an ovoid shape. The circular shape is more preferred for more comfort in the vaginal wall.

Receptacle 3 includes a body 4 having a curved longitudinal shape and a base 5 corresponding in particular to the base of the container. Body 4 is in particular the part configured to conform to the vaginal wall. Base 5 is the part where the first menstrual flows fall, and cup 1 is filled from base 5 towards opening 2 on an ongoing basis of said flows.

The receptacle may include a plane of symmetry or preferably an axis of symmetry, in particular a rotational axis of symmetry. This axis is at the center of receptacle 3.

Menstrual cup 1 extends longitudinally from opening 2 towards base 5. Cup 1 may also extend laterally, but the longitudinal axis is considered as the one going from opening 2 towards base 5 of menstrual cup 1.

Menstrual cup 1 has an internal surface 6 in the concavity of receptacle 3, and an external surface 7 in the convexity of receptacle 3.

As per the invention, body 4 includes a number of hollow longitudinal grooves 8 on internal surface 6 of body 4.

Advantageously, the number of solid longitudinal grooves allows increasing the containment capacity of menstrual cup 1 without increasing the maximal diameter of menstrual cup 1.

As per one variant, cup 1 also includes a number of solid longitudinal grooves 9 on external surface 7 of body 4.

Advantageously, the number of solid longitudinal grooves 9 allows counteracting tonicity impairments of the perineum or the vaginal wall or their weakening. Menstrual cup 1 thus holds in place better in the vaginal cavity in particular because of the increase of the surface contact between cup 1 and the vaginal wall because of said solid groove.

As per one variant, said number of solid longitudinal grooves 9 on external surface 7 matches said number of hollow longitudinal grooves 8 on internal surface 6. Advantageously, this feature allows making the hollow grooves 8 and the solid grooves 9 of a significant size and thus improving the efficiency in containment and the holding in the vaginal wall.

As per one variant, cup 1 includes four hollow longitudinal grooves 8 that match four solid grooves 9. More specifically, these grooves are distributed regularly on the periphery of body 4.

A regular distribution of grooves 8; 9 allows benefitting from the advantage of said hollow groove 8 and/or said solid groove 9 in several places of menstrual cup 1.

Providing four grooves allows having a good compromise between the number of them and their section.

As per one variant, at least one groove has a tubular element shape having a thickness corresponding to around one third of the thickness of the opening. The grooves measures around ten millimeters, for example. Advantageously, the grooves have a significant size which allow benefitting fully from the effect on containment and/or holding, in particular on the walls having tonicity or weakening defects.

More generally, at least one groove 8, 9 may have a curved or angular section.

The general shape of the groove may be flared, in the shape of a pear, or ovoid. For example, the grooves may have a thin size near the opening and a wider size near the base in order to improve the holding of the menstrual cup in the vaginal cavity more. A curved section may be combined with a general shape not being circular. For example, a serpentine shape may be envisioned.

In particular, the four hollow and solid grooves preferably have the same shape.

As per one variant, cup 1 includes a flared section 9a towards the top between body 4 and opening 2, in particular flange 2a. The flared section 9a includes in particular a tulip shape. The flared section 9a allows increasing the containment of menstrual cup 1 more and also having better holding in the vaginal cavity because of the flared shape resisting the removal of menstrual cup 1.

As per one variant, the flared section 9a has a diameter increase of more than around 25% between the maximal diameter of the body and the external diameter of the flared section, preferably more than 50% and more preferentially less than 80%. In the variant illustrated in FIGS. 5 through 8, a diameter increase of 66%, from 30 mm to 50 mm, was done and gives very good results.

The flared shape was studied to be adapted perfectly to the vaginal anatomy and the upper flange in a ring shape is reinforced in order to optimize the opening of cup 1 and open holding allowing the seal with the vaginal wall.

In order to have dependable protection, the choice of the menstrual cup is a function of the tonicity of the perineum. From there, two criteria are to be taken into consideration: the diameter of the cup and its relative flexibility. In fact, this cup may be set more or less supple, even rigid.

Several sizes of diameters of menstrual cup 1 may be envisioned in order to be able to be adapted to the majority of women according to their vaginal anatomy. For example, the external diameter may be 41 mm, 51 mm, or 56 mm. Cup 1 of FIG. 1 has an external diameter of 41 mm and an internal diameter of 31 mm. The cup from FIG. 5 has a diameter of 56 mm along opening 2 and an internal diameter of 31 mm along body 4.

Menstrual cup 1 may include a stem 11 integral with base 5. Stem 11 preferably includes reliefs 12 at regular intervals. Stem 11 is adjusted at the exit of the vaginal cavity when menstrual cup 1 is placed there. A part extending to the exterior of the vagina may be cut out and the remaining part is used for removing the menstrual cup.

Menstrual cup 1 may include orifices 13 below opening 2, in particular below flange 2a, which allows decreasing the plunger effect between the cup and the vaginal wall.

Preferably, menstrual cup 1 is made out of thermoplastic material that is non-irritating to the vaginal wall. More preferentially, the material of the menstrual cup is configured to allow bending cup 1, placing it into the vaginal cavity and letting it resume its initial shape. For example, the material includes medical silicon. At least one common polymer may be used, or a mixture of polymers. The elastomer thermoplastic TPE and thermoplastic polyurethane TPU families polymers may be chosen. Medical use silicon material is preferred to have more comfort of use.

Once placed into the vaginal cavity, the receptacle comes into contact with the vaginal wall and the menstrual flows enter through the opening and are deposited into the receptacle.

The preferred menstrual cup 1 measures around 5 cm in length and from 3 to 5 cm in width depending on the presence or absence of the flared shape.

The capacity of the preferred menstrual cup is around 15 to 50 ml depending on the presence or the absence of the flared shape.

Menstrual cup 1 as per the invention may be held in the vaginal cavity in spite of abundant periods for a maximal duration of use generally set at around 12 hours in order to avoid toxic shock syndrome. A known menstrual cup without grooves or flared shape has significantly lesser containment.

After use, menstrual cup 1 may be washed, placed into a storage case (b) and disinfected (c) in a microwave oven.

Thus, the invention also concerns a kit including a menstrual cup 1 as described above configured to be resistant to microwaves, and a storage container 13 that is resistant to microwaves. The corresponding disinfection method is also part of the invention.

The invention also concerns a production process of a menstrual cup 1 as described above, including a forming step of at least one solid longitudinal groove and at least one hollow longitudinal groove, characterized by the shaping of said grooves through a mold including a matching longitudinal groove. In one variant, the shaping includes in particular a polymerization of the menstrual cup material. More specifically, a male mold and a female mold are used, and the polymerization is done between the two molds.

As per another feasible variant, the menstrual cup may be made by 3D printing through a 3D printer known to skilled persons.

I claim:

1. A menstrual cup, comprising:
a receptacle being comprised of:
a body having a curved longitudinal shape so as to define an internal concave surface and an external convex surface;
an upper opening at an end of said body; and
a base at an opposite end of said body;
a hollow longitudinal groove extending from said upper opening toward said base on the internal surface; and
a solid longitudinal groove extending from said upper opening toward said base on the external surface so as to match said hollow longitudinal groove along the internal surface.

2. The menstrual cup, as per claim 1, wherein at least one of said hollow longitudinal groove and said solid longitudinal groove has a curved or angular section, and wherein said solid longitudinal groove has a curved or angular section.

3. The menstrual cup, as per claim 1, wherein at least one of said hollow longitudinal groove and said solid longitudinal groove has a serpentine shape.

4. The menstrual cup, as per claim 1, wherein said body is comprised of a flared section towards said end of said body at said upper opening.

5. The menstrual cup, as per claim 4, wherein said flared section has an initial diameter toward said opposite end of said body and an external diameter toward said end of said body at said upper opening, and wherein said initial diameter increases at least 25% to said external diameter.

6. The menstrual cup as per claim 1, further comprising:
a plurality of hollow longitudinal grooves, said hollow longitudinal groove being one of said plurality of hollow longitudinal grooves, each hollow longitudinal groove of said plurality of hollow longitudinal grooves extending from said upper opening toward said base on the internal surface, and
a plurality of solid longitudinal grooves, said solid longitudinal groove being one of said plurality of solid longitudinal grooves, each solid longitudinal groove of said plurality of solid longitudinal grooves extending from said upper opening toward said base on the external surface.

7. The menstrual cup, as per claim 6, wherein at least one hollow longitudinal groove of said plurality of hollow longitudinal grooves has a sectional tubular shape having a sectional tubular thickness, and wherein said sectional tubular thickness is one third of a thickness of said receptacle at said upper opening.

8. The menstrual cup, as per claim 6, wherein each hollow longitudinal groove of said plurality of hollow longitudinal grooves matches a corresponding solid longitudinal groove of said plurality of solid longitudinal grooves, and
wherein said plurality of solid longitudinal grooves are distributed regularly [on the] around a periphery of said body.

9. The menstrual cup, as per claim 8 wherein said plurality of hollow longitudinal grooves is comprised of four hollow longitudinal grooves, and
wherein said plurality of solid longitudinal grooves is comprised of four solid longitudinal grooves.

10. A menstrual cup, comprising:
a receptacle being comprised of:
a body having a curved longitudinal shape so as to define an internal concave surface and an external convex surface;
an upper opening at an end of said body; and
a base at an opposite end of said body;
a hollow longitudinal groove extending from said upper opening toward said base on the internal surface; and
a solid longitudinal groove extending from said upper opening toward said base on the external surface so as to match said hollow longitudinal groove along the internal surface,
wherein at least one of said hollow longitudinal groove and said solid longitudinal groove has a pear or ovoid flared shape.

11. A kit, comprising:
a menstrual cup, being configured in order to be resistant to microwaves and comprising:
a receptacle being comprised of:
a body having a curved longitudinal shape so as to define an internal concave surface and an external convex surface;

an upper opening at an end of said body; and
a base at an opposite end of said body;
a hollow longitudinal groove extending from said upper opening toward said base on the internal surface; and
a solid longitudinal groove extending from said upper opening toward said base on the external surface so as to match said hollow longitudinal groove along the internal surface; and
a storage container resistant to microwaves.

* * * * *